US010322954B2

(12) United States Patent
Gooch

(10) Patent No.: US 10,322,954 B2
(45) Date of Patent: Jun. 18, 2019

(54) ANTIMICROBIAL DEVICE AND MATERIALS FOR FLUID TREATMENT

(75) Inventor: Jan W. Gooch, Atlanta, GA (US)

(73) Assignee: HYDRO AIR GLOBAL, LLC, Lawrenceville, GA (US)

(*) Notice: Subject to any disclaimer, the term of this patent is extended or adjusted under 35 U.S.C. 154(b) by 504 days.

(21) Appl. No.: 12/622,456

(22) Filed: Nov. 20, 2009

(65) Prior Publication Data

US 2010/0125105 A1    May 20, 2010

Related U.S. Application Data

(60) Provisional application No. 61/116,585, filed on Nov. 20, 2008.

(51) Int. Cl.
| | | |
|---|---|---|
| A01N 37/52 | (2006.01) | |
| A61K 9/14 | (2006.01) | |
| A61K 31/74 | (2006.01) | |
| C02F 1/50 | (2006.01) | |
| A01N 47/44 | (2006.01) | |
| A01N 25/10 | (2006.01) | |
| C02F 1/00 | (2006.01) | |

(52) U.S. Cl.
CPC ............ *C02F 1/50* (2013.01); *A01N 25/10* (2013.01); *A01N 47/44* (2013.01); *C02F 1/002* (2013.01); *C02F 2303/04* (2013.01)

(58) Field of Classification Search
USPC ............... 514/634, 635, 740, 741, 772.1
See application file for complete search history.

(56) References Cited

U.S. PATENT DOCUMENTS

| | | | | |
|---|---|---|---|---|
| 4,343,853 | A * | 8/1982 | Morrison | A41D 31/00 |
| | | | | 428/905 |
| 5,762,797 | A | 6/1998 | Patrick et al. | |
| 6,238,575 | B1 | 5/2001 | Patil | |
| 6,540,916 | B2 | 4/2003 | Patil | |
| 6,551,608 | B2 | 4/2003 | Yao | |
| 6,849,214 | B2 | 2/2005 | Patil | |
| 6,854,601 | B2 | 2/2005 | Patil | |
| 7,267,789 | B2 * | 9/2007 | Chhabra et al. | 264/115 |
| 7,771,743 | B1 | 8/2010 | Luthra et al. | |
| 7,850,982 | B2 * | 12/2010 | Stopek et al. | 424/400 |
| 2004/0214495 | A1 | 10/2004 | Foss et al. | |
| 2005/0258093 | A1 | 11/2005 | Cueman et al. | |
| 2006/0051385 | A1 | 3/2006 | Scholz | |
| 2007/0006391 | A1* | 1/2007 | Ghosh et al. | 8/115.51 |
| 2007/0044801 | A1* | 3/2007 | Mathis | A41D 13/11 |
| | | | | 128/206.19 |
| 2007/0048344 | A1 | 3/2007 | Yahiaoui et al. | |
| 2007/0048356 | A1 | 3/2007 | Schorr et al. | |
| 2007/0048358 | A1 | 3/2007 | Schorr et al. | |
| 2007/0270552 | A1 | 11/2007 | Zheng | |
| 2010/0125105 | A1 | 5/2010 | Gooch | |
| 2010/0234815 | A1 | 9/2010 | Do et al. | |

FOREIGN PATENT DOCUMENTS

| | | |
|---|---|---|
| EP | 1983026 A1 | 10/2008 |
| JP | 2001159029 A | 6/2001 |
| WO | 8602561 A1 | 5/1986 |
| WO | WO 86/02561  * | 5/1986 |
| WO | 2007016481 A1 | 2/2007 |
| WO | 2007078203 A1 | 7/2007 |
| WO | 2009064767 A2 | 5/2009 |
| WO | 2010025224 A1 | 3/2010 |

OTHER PUBLICATIONS

Tallury et al., Dental Materials, vol. 23, 2007, pp. 404-409.*
Laing, Raechel M., Protection Provided by Clothing and Textiles Against Potential Hazards in the Operating Theatre, International J. of Occupational Safety and Ergonomics (JOSE) 2008, vol. 14, No. 1, pp. 107-115.
Behery, Hassan M., Characterization and Testing of Nonwovens with Emphasis on Absorbency, Nonwovens-Theory, Process, Performance & Testing 2007, Chapter 10, pp. 207-228.
International Search Report and Written Opinion PCT/US2010/052608 dated Feb. 3, 2011.
Tallury et al., Poly(ethylene-co-vinyl acetate) Copolymer Matrix for Delivery of Chlorhexidine and Acyclovir Drugs for Use in the Oral Environment: Effect of Drug Combination, Copolymer Composition and Coating on the Drug Release Rate, Dental Materials, vol. 23, 2007, pp. 404-409.

* cited by examiner

*Primary Examiner* — Shobha Kantamneni

(57) ABSTRACT

Compositions comprising miscible blends of antimicrobial bisguanide compounds with certain thermoplastic polymers are provided. These antimicrobial polymeric materials may be further processed into particulate or fiber form for use in fluid treatment devices and processes. The antimicrobial bisguanide compound, such as chlorhexidine, is distributed at the molecular level within at least one thermoplastic polymer, such as a polyolefin, in which the antimicrobial bisguanide compound is soluble to form a miscible blend, which may be from about 1% to about 25% by weight antimicrobial bisguanide compound. The antimicrobial polymeric materials may be secured in a device for antimicrobial treatment of a fluid. The devices may comprise a housing having at least one inlet orifice and at least one outlet orifice, the antimicrobial polymeric material being secured within the house and configured to contact a fluid flowing through the housing between the inlet orifice and the outlet orifice.

8 Claims, 9 Drawing Sheets

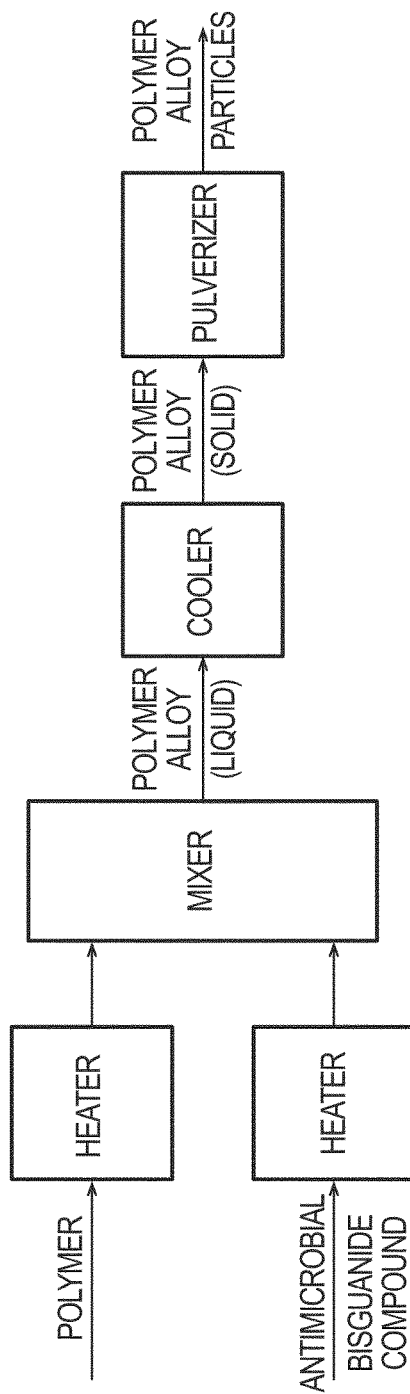
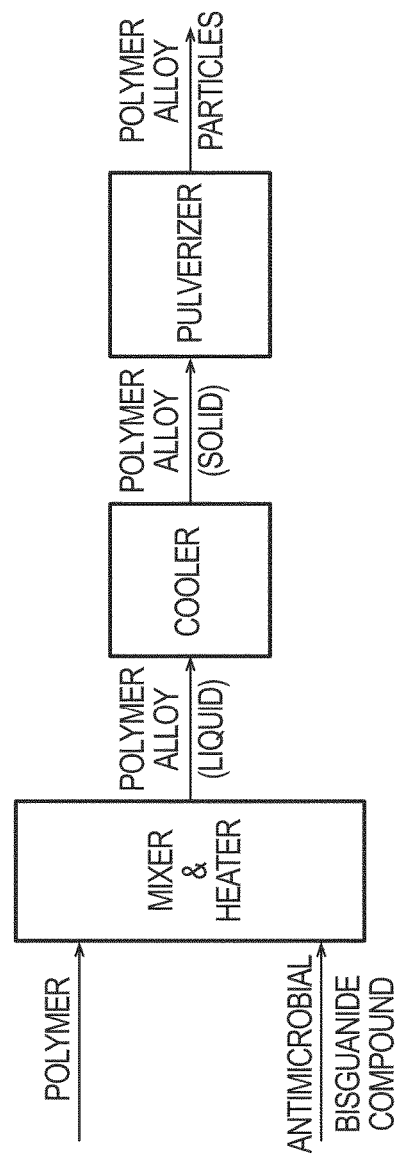
FIG. 4A
FIG. 4B

ANTIMICROBIAL DEVICE AND MATERIALS FOR FLUID TREATMENT

CROSS-REFERENCE TO RELATED APPLICATIONS

This application claims benefit of U.S. Provisional Application No. 61/116,585, filed Nov. 20, 2008. This application is incorporated herein by reference.

BACKGROUND

This disclosure is generally in the field of antimicrobial polymeric materials and devices useful in the purification of fluids.

There remains a need for devices and methods to eliminate microorganisms from fluids for various applications, including the provision of safe or potable drinking water and breathable purified air. Many different methods are currently used for the purification of fluids. Representative examples include distillation, ion-exchange, chemical adsorption, filtering, and retention. Oftentimes, a number of different techniques must be combined to provide complete purification of fluids. These techniques can be costly, energy inefficient, and require significant technical expertise. Unfortunately, many low cost purification techniques do not adequately treat or remove harmful biological contaminants, bacteria, and viruses.

The U.S. Environmental Protection Agency (EPA) has set forth minimum standards for acceptance of a device proposed for use as a microbiological water filter. Common coliforms, represented by the bacteria E. coli and Klebsiella terrigena, must show a minimum 6-log reduction (99.9999% of organisms removed) from an influent concentration of $1 \times 10^7$ per 100 mL of water. Common viruses, represented by poliovirus 1 (LSc) and rotavirus (Wa or SA-11), which show a resistance to many treatment processes, must show a minimum 4-log reduction (99.99% of organisms removed), from an influent concentration of $1 \times 10^7$ per 100 mL of water. Cysts, such as those represented by Giardia muris or Giardia lamblia, are widespread, disease-inducing, and resistant to most forms of chemical disinfection. A device claiming cyst-removal must show a minimum 3-log reduction (99.9% of cysts removed) from an influent concentration of $1 \times 10^6$ per L or $1 \times 10^7$ per L.

Various water soluble antimicrobial chemical agents are known in the art. Representative examples of such conventional materials include soaps/detergents, surfactants, acids, alkalis, heavy metals, halogens, alcohols, phenols, oxidizing agents and alkylating agents. Most of these agents chemically alter (e.g., by an oxidation reaction, etc.) the cellular structure of microbes to inactivate them. Strong oxidants, such as phenols and hypochlorites, may effectively negate the potential threat of all microorganisms in water; however, unacceptable residual levels of these agents and/or their byproducts remain in the treated water and generally must be removed before the treated water can be consumed or used in other applications.

One conventional biocompatible antimicrobial agent is chlorhexidine. Chlorhexidine is a 1,6-di (4-chlorophenyl-diguanido) hexane having the chemical formula:

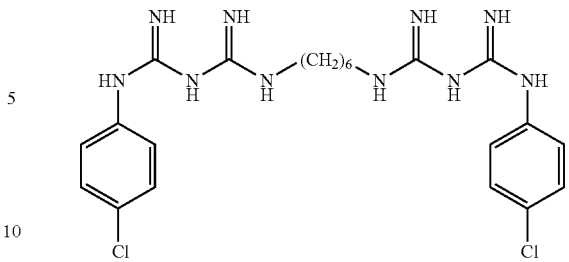

The IUPAC name for chlorhexidine is N,N"Bis(4-chlorophenyl)-3,12-diimino-2,4,11,13-tetrazatetradecanediimideamide. Chlorhexidine has a high level of antibacterial activity and low mammalian toxicity. Historically, chlorhexidine has been used in fluid treatment only in its soluble salt forms. Chlorhexidine salts, however, have an extremely bitter taste that must be masked in formulations intended for oral use. The rate of reaction for the soluble chlorhexidine salts or its conventional derivatives is second-order, as the reaction depends on both the concentration of chlorhexidine and the active sites of microorganisms. It would be desirable to provide an antimicrobial material which functioned effectively as a zero order reaction.

One conventional antimicrobial system for fluid treatment that does not involve the use of water soluble antimicrobial agents utilizes ultraviolet (UV) radiation. Such systems, however, require a source of electric power, are costly, and may not effectively inactivate microorganisms in a range of fluid types.

Accordingly, there remains a need for inexpensive and biocompatible antimicrobial materials and devices that can effectively inactivate microorganisms in fluids. It would be desirable for the antimicrobial material to work effectively as an antimicrobial material without being water soluble, so as not to detrimentally impact the quality of the aqueous fluid to be filtered and in order to avoid having to remove the residual antimicrobial material or by products from the treated fluid. It would be further desirable for the material to be readily adaptable for use in various conventional flow-through fluid filtration/purification systems, without the need for an additional power source. Desirably, the purification material would significantly exceed the minimum EPA requirements for designation as a microbial water purifier such that it is suitable for consumer and industry point-of-use applications.

SUMMARY

Novel antimicrobial materials, devices, and methods are provided herein. The antimicrobial polymeric material may comprise a composition comprising a miscible blend of at least one antimicrobial bisguanide compound blended with at least one thermoplastic polymer. The miscible blend may comprise from about 1% to about 25% by weight of the at least one antimicrobial bisguanide compound. In one embodiment, the antimicrobial bisguanide compound comprises chlorhexidine and the at least one thermoplastic polymer comprises a polyolefin.

In another aspect, methods are provided for making an antimicrobial polymeric material. In one embodiment, the method comprises: melting an antimicrobial bisguanide compound and a thermoplastic polymer with which the antimicrobial bisguanide compound is miscible; mixing the melted antimicrobial bisguanide compound and the melted thermoplastic polymer to form a miscible blend of the antimicrobial bisguanide compound dispersed in the thermoplastic polymer, and cooling the miscible blend to solidify the blend. In one embodiment, the method further comprises processing the solidified blend into a particulate form. In still another embodiment, the miscible blend is extruded into fibers before solidifying the miscible blend.

In still another aspect, devices for antimicrobial fluid treatment are provided. In one embodiment, the device comprises a housing having at least one inlet orifice and at least one outlet orifice and an antimicrobial material secured within the housing and configured to contact a fluid flowing through the housing between the inlet orifice and the outlet orifice. The antimicrobial material desirably comprises a miscible blend of an antimicrobial bisguanide compound blended with at least one thermoplastic polymer, wherein the miscible blend is from about 1% to about 25% by weight antimicrobial bisguanide compound. Desirably, the antimicrobial bisguanide compound comprises chlorhexidine and the at least one thermoplastic polymer comprises a polyolefin. In one aspect, the miscible blend is in the form of loose particles. In another aspect, the miscible blend is in the form of a porous monolithic structure, such as a sintered disk or block. In still another aspect the miscible blend is in the form of a nonwoven material.

Also provided is a method for inactivating microbiological contaminants in a fluid comprising contacting the fluid with a miscible blend of an antimicrobial bisguanide compound and at least one thermoplastic polymer, wherein the miscible blend is from about 1% to about 25% by weight antimicrobial bisguanide compound. The fluid desirably flows through pores in or among an aggregation of particles comprising the miscible blend.

BRIEF DESCRIPTION OF THE DRAWINGS

FIGS. 4A and 4B are illustrations of a method for preparing an antimicrobial polymeric material according to some embodiments.

DETAILED DESCRIPTION

Solid solutions of antimicrobial bisguanide compounds blended with certain thermoplastic polymers have been developed to obtain antimicrobial polymeric materials. They may be processed into particulate form for use as or in fluid treatment devices and processes. The alloy material advantageously may be easily processed into a variety of physical forms for use in fluid treatment.

The antimicrobial bisguanide compound, such as chlorhexidine, is distributed at the molecular level within at least one thermoplastic polymer, such as a polyolefin in which the antimicrobial bisguanide compound is soluble. In one embodiment, these components are melted and blended together to form a miscible blend, sometimes herein called a polymer alloy. In one embodiment, the blend is cooled to solidify the blend and then the blend is processed into a particulate form. The blend particles can be provided in a porous disk form or otherwise incorporated into a particle bed for contacting a fluid flowing therethrough. Passage of a fluid in need of antimicrobial treatment through pores in and among the polymer alloy particles inactivates microorganisms in the fluid. In another embodiment, the blend is extruded into fibers for forming nonwoven and woven materials.

The alloy material provides an improvement over the conventional soluble bisguanide salts (e.g., chlorhexidine gluconate, etc.), over conventional crystalline bisguanide base forms (e.g., chlorhexidine, etc.), and over bisguanide hydrates, which are described in U.S. Pat. No. 7,427,409. The alloy material also provides an improvement over prior art combinations of polymers with soluble bisguanide salts, crystalline bisguanide base forms, and bisguanide hydrates by providing an antimicrobial agent in a form which is immobilized with a polymer and which is water-insoluble. For example, the alloy materials provided herein overcome problems associated with the thermal degradation of the antimicrobial bisguanide compound during processing, thereby retaining the material's antimicrobial activity. In addition, the antimicrobial bisguanide compound remains immobilized within the thermoplastic polymer, thereby avoiding problems associated with leaching of the antimicrobial bisguanide compound from the alloy material.

Figure 1A:
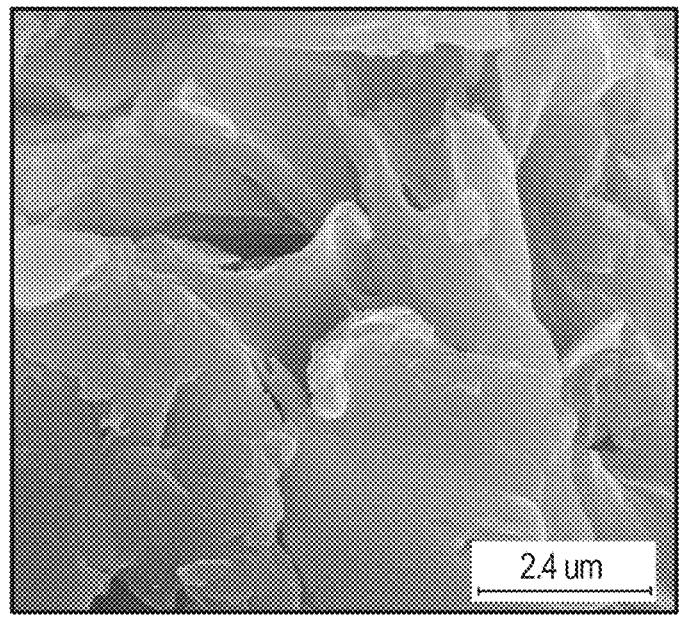
FIGS. 1A and 1B are SEM images of a chlorhexidine-polyethylene composition.
Figure 1B:
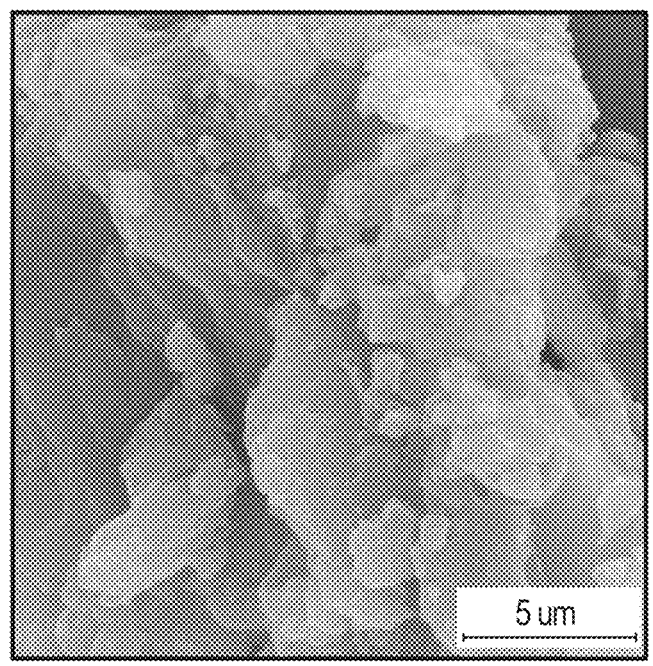

The antimicrobial bisguanide compounds lose their natural morphology upon preparation of the antimicrobial polymeric material. For example, a scanning electron micrograph (FIGS. 1A and 1B) of the cross-section of one embodiment of the antimicrobial polymeric material, a chlorhexidine-polyethylene composition, shows no evidence of the crystalline form of the bisguanide. Not wishing to be bound by any theory, it is believed that the loss of the typical orthorhombic structure of the antimicrobial bisguanide (e.g., chlorhexidine) within the polymer material is due to its chemical and physical compatibility with certain thermoplastic polymers. This compatibility allows for the molecular dispersion of the bisguanide molecules with the polymer molecules, thereby preventing the bisguanide molecules from reforming their natural lattice structures.

The present antimicrobial polymeric materials, devices, and methods operate by physical/mechanical contact between the blend material and the fluid to be treated. Microorganisms in the fluid can be inactivated by contact (e.g., transient contact) with the blend material. Inactivation of the microorganisms is a physical phenomenon and need not (but optionally could) further include removal of the skeletal remains of the inactivated microorganisms from the fluid, e.g., by filtration.

As used herein, the term "antimicrobial polymeric material" refer to a blend that comprises at least one antimicrobial bisguanide compound in a solid solution with at least one thermoplastic polymer, wherein the resulting material exhibits antimicrobial activity. The antimicrobial polymeric material also may be referred to herein as a "purification material."

The present antimicrobial polymeric materials, devices, and methods of use may be further understood with reference to the following description and accompanying figures.

The Antimicrobial Devices and Methods of Use

Devices for antimicrobial fluid treatment are provided that are designed to allow, or force, a fluid to be treated to flow through a porous structure that includes or consists of the antimicrobial polymeric material. Accordingly, the antimicrobial polymeric material may be in essentially any structure or form that provides sufficient contact with the fluid to be treated. For example, the structure may be in a loose granular or particulate form, or the structure may be in a unitary form in various geometric configurations, such as sheets, films, disks, rectangular blocks, closed cylinders, cylinders having one or more apertures (or bores) extending therethrough, and the like. The structure also may be in the form of a collection of woven or non-woven fibers comprising the antimicrobial polymeric material.

In one aspect, a device for antimicrobial fluid treatment is provided that includes a collection of particles which comprise a miscible blend of one or more antimicrobial bisguanide compounds blended with at least one thermoplastic polymer. The antimicrobial bisguanide and thermoplastic polymer may be combined in any amount in which the resulting antimicrobial polymeric material has sufficient antimicrobial activity and retains the structural integrity or porosity needed for a particular use of the antimicrobial polymeric material. Thus, the antimicrobial bisguanide compound should be present in an amount sufficient to facilitate contact between the antimicrobial polymeric material and the fluid in need of treatment. In one embodiment, the miscible blend is from about 1% to about 25% by weight antimicrobial bisguanide compound. For example, between about 1% and about 10% by weight, or between about 1% and about 5% by weight. In another embodiment, the miscible blend is from about 5% to about 15% by weight antimicrobial bisguanide compound. In still other embodiments, the blend is from about 10% to about 25% by weight. Greater or lesser amounts of antimicrobial bisguanide compound may be selected for use in the antimicrobial polymeric material, depending for example on the required mechanical characteristics (e.g., load bearing characteristics, porosity, etc.) that are specified for the particular fluid treatment application in which the antimicrobial polymeric material is to be used.

In one embodiment, the particles have a volume average diameter from about 400 mesh (37 micron) to about 20 mesh (840 micron). For example, in some embodiments, the particles may have a volume average diameter from about 40 mesh (<420 micron) to about 325 mesh (<44 micron) or from about 80 mesh (<177 micron) to about 200 mesh (<74 micron).

In one embodiment, the particles are porous. For example, a pore forming agent known in the art may be incorporated into the fluidized blend prior to solidification. The pore forming agent may be a gas or a volatile salt, for example.

In one embodiment, the particles are in a fiber or fibrid form. For example, the fluidized blend may be extruded or spun to yield fibers for use in a nonwoven material or woven material.

The pore size and physical dimensions of the purification material (at both the particle level and device level) may be manipulated for different fluid treatment applications. Changes in these variables may be selected to accommodate for various flow rates and back-pressure. Similarly, those skilled in the art will recognize that variations in the composition of the purification material will likewise effect the material properties of the purification material.

Figure 2:
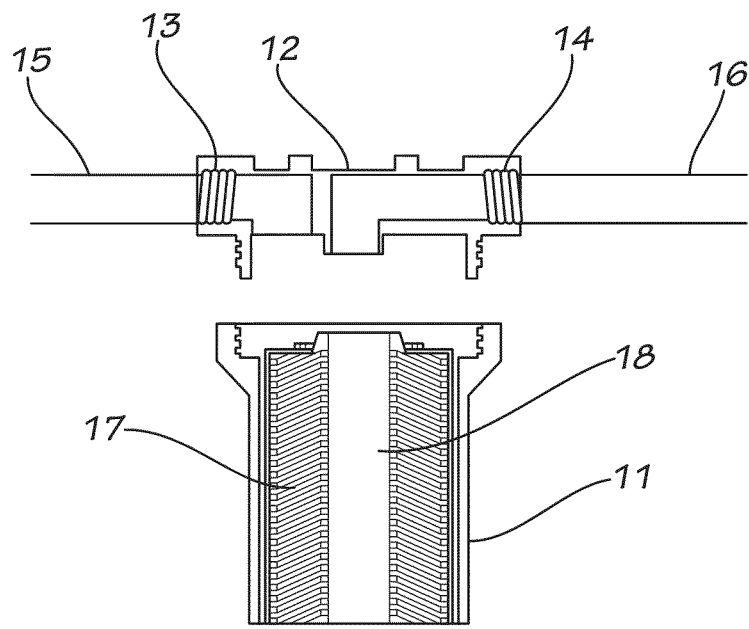
FIG. 2 is a cross-sectional view illustrating one embodiment of a fluid treatment device comprising an antimicrobial polymeric material.

One embodiment of a fluid treatment device comprising the present antimicrobial polymeric materials is illustrated in FIG. 2. In one embodiment, the device includes a housing 11 mated with a cap 12, the housing 11 having at least one inlet orifice 13 and at least one outlet orifice 14, wherein the antimicrobial polymeric material 17 is secured in the house in fluid communication between the inlet orifice and the outlet orifice. A fluid supply conduit may be joined to the inlet orifice 12, to deliver untreated fluid into the device, and a fluid discharge conduit may be joined to the outlet orifice 14, to conduct treated fluid from the device. The fluid may pass into the housing 11 and be forced through the porous purification material 17, which is in the shape of hollow cylinder with an axial bore 18, by the pressure of the fluid flow. The treated fluid then passes into the axial bore 18 which connects to the outlet orifice 14. In one embodiment, the antimicrobial polymeric material 17 is in the form of particles in a loose form, e.g., forming a packed bed within the housing. In another embodiment, the antimicrobial polymeric material 17 is in the form of a porous monolithic structure. For example, the porous monolithic structure may be a sintered disk or block. In still another embodiment, the antimicrobial polymeric material 17 is in the form of a nonwoven or woven porous structure (e.g., a filament wrapped filter prepared from spun fibers having the desired tightness and porosity that are wrapped on a suitable core material).

In one embodiment, the antimicrobial bisguanide compound comprises chlorhexidine or a chlorhexidine hydrate. With the chlorhexidine hydrate, it should be appreciated that the process of making the antimicrobial polymeric material may result in the loss of the water molecule(s) from the chlorhexidine hydrate, to yield the neat form of chlorhexidine in the antimicrobial polymeric material. In a preferred embodiment, the antimicrobial bisguanide compound is in an amorphous form in the blend. In one embodiment, the thermoplastic polymer includes one or more polyolefins. Polyethylene is a preferred thermoplastic polymer in the blend.

Figure 3:
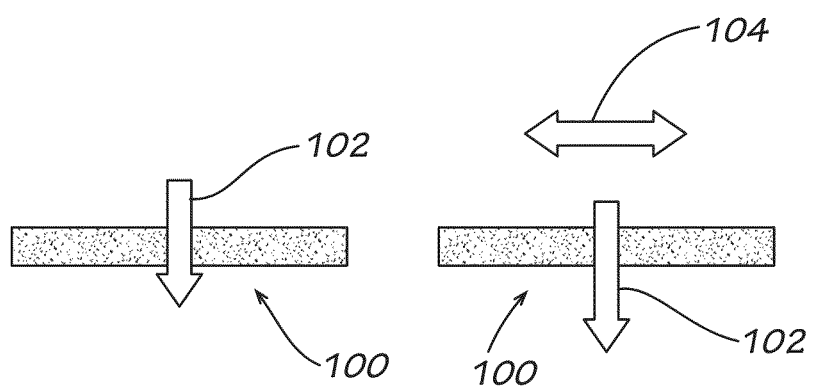
FIGS. 3A and 3B are schematic views of one embodiment of an antimicrobial polymeric material in the form of a sheet or film.

FIGS. 3A-3B show two embodiments where the purification material described herein is in the form of a sheet or film. The antimicrobial polymeric material 100 can be used with normal flow-through of a fluid 102 through the antimicrobial polymeric material (FIG. 3A). Alternatively, an antimicrobial polymeric material 100 can be used with cross-flow of a fluid 104 across the antimicrobial polymeric material with fluid 102 flowing through the antimicrobial polymeric material (FIG. 3B). The cross-flow fluid 104 sweeps across the surface of the antimicrobial polymeric material 100, which may decrease the level of particulate matter deposited thereon.

In another embodiment, the purification material is in the form a porous monolithic structure. The structure can be made by compression molding a particulate form of the antimicrobial polymeric material or by extrusion molding the antimicrobial polymeric material. The compression molding advantageously and desirably may be molded at ambient temperature conditions, e.g., without input of heat. In another embodiment, the particulate form of the antimicrobial polymeric material is molded at other non-ambient temperatures. Those skilled in the art will appreciate that such temperatures should be sufficiently below the degradation temperature of the antimicrobial bisguanide in order to avoid impairing its antimicrobial activity. The heatless pressure causes the particles to aggregate together, or fuse into a monolithic structure, with no loose particles, while retaining its porosity. The purification material may have a melting temperature below its decomposition temperature, allowing it to be molded into different physical shapes without undesirably altering the compound's chemical or structural integrity.

In still another embodiment, the present antimicrobial polymeric material is coated on an inert carrier substrate. For example, the substrate may be in the form of glass or ceramic beads (e.g., spheres or other shapes) or other loose packing objects which increase the active/available surface area of the antimicrobial polymeric material.

In still another embodiment, the present antimicrobial polymeric material is in the form of a woven or nonwoven material. Non-woven materials, as used herein, include sheet or web-based structures prepared by bonding together fiber or filaments by chemical, mechanical, heat or solvent treatments known in the art. Such materials may comprise flat, porous sheets made directly from fibers, molten plastic, or plastic film. Those of skill in the art will appreciate that unlike woven materials, nonwoven materials are not made by weaving or knitting, and do not require that the fibers be converted into yarn. Woven materials, as used herein, include sheet or web-based structures that are prepared by weaving or knitting fibers or filaments that may be converted into yarn. Nonwoven and woven materials comprising the purification material may be engineered to have particular properties, structures, or forms depending upon the desired application using methods known in the art. Methods of preparing such materials are described, for example, in U.S. Pat. Nos. 6,548,431; 5,853,883; 5,853,641; and 5,632,944 and U.S. Patent Publication No. 2004/0097158, the disclosures of which are incorporated herein by reference. The processing temperature of any process should be sufficiently below the degradation temperature of the antimicrobial polymeric materials such that there is substantially no degradation of the antimicrobial polymeric materials.

The particles and other devices formed by molecularly distributing the antimicrobial bisguanide compound with the polymer are believed to have surface properties that are antimicrobial due to the presence of antimicrobial bisguanide compound which is immobilized with the polymer chain network. The surfaces of these particles should retain their antimicrobial activity until they are fouled, which is a common mode of failure for any surface active solid particle known to those of skill in the art. Accordingly, in particular embodiments, the antimicrobial polymeric material is used in combination with other materials and devices known in the art of fluid treatment.

For instance, the purification material or device may be used in a process in series with a filtration device, for example as a pretreatment to remove larger-scale particulate matter and/or as a post treatment to filter out skeletal remains of inactivated microorganisms. As another example, the fluid may be treated using methods, materials, and systems known in the art to remove other organic or inorganic matter or solutes. Suitable filter media for pre-filtration are described for example in U.S. Pat. Nos. 6,187,192; 6,180, 016; 6,957,743; 6,833,075; and 6,861,002; and in U.S. patent application Ser. Nos. 10/276,274 and 10/467,679.

In another aspect, a method is provided for inactivating microbiological contaminants in a fluid. The method may include contacting a fluid in need of treatment with particles that comprise a miscible blend of an antimicrobial bisguanide compound blended with at least one thermoplastic polymer. The contacting step may include flowing the fluid through pores in or among a collection, or aggregation, of the particles.

1. The Antimicrobial Bisguanide Compound.

Suitable bisguanide compounds exhibit antimicrobial activity. The term "antimicrobial activity" refers to the property or capability of a material to inactivate microorganisms. Non-limiting examples of microorganisms include bacteria, fungi, and viruses. This "inactivation" renders the microorganism incapable of reproducing and therefore incapable of infecting other organisms and occurs by disruption of the bacteria, fungi or protozoa membrane, or by denaturization of the protein such as that which forms the protective capsid for viruses. While not wishing to be bound by any theory, it is believed that the antimicrobial activity of the bisguanide compound is due to its highly cationic nature. Generally, microorganisms have cell membranes composed of lipids and proteins. When the microorganisms are exposed to the bisguanide compositions, the microorganisms experience a change in surface charge in the cell membrane sufficient to disrupt the cell membrane and render the microorganisms incapable of reproduction In one embodiment, the bisguanide compound exhibits broad spectrum antimicrobial activity. The term "broad spectrum antimicrobial activity" refers to the property or capability of a material to inactivate numerous different, or substantially all, types of microorganisms including bacteria (and its corresponding spores), fungi, protozoa and viruses. An antimicrobial agent that inactivates only a select group of microorganisms (e.g., either only gram positive cells or only gram negative cells) does not have broad spectrum antimicrobial activity.

In a preferred embodiment, the antimicrobial bisguanide compound is water insoluble The term "water insoluble" refers to substantial insolubility in aqueous fluids, particularly aqueous fluids having a pH in the range of about 3 to about 11, such as between about 4 and about 9, and particularly in the range of 6.0 to 8.0. Substantial insolubility may be indicated by measuring less than 0.01% (weight by volume) of the bisguanide compound using conventional detection methods and tools.

In one embodiment, the antimicrobial bisguanide compound is chlorhexidine.

In another embodiment, the antimicrobial polymeric materials include at least one of the bisguanide hydrates described in U.S. Pat. No. 7,427,409 or in co-pending U.S. patent application Ser. No. 12/016,550, the disclosures of which are incorporated herein by reference. Tautomers of such bisguanide compounds may also be suitable.

In one embodiment, the bisguanide compound includes a bisguanide hydrate having the chemical formula (Formula I):

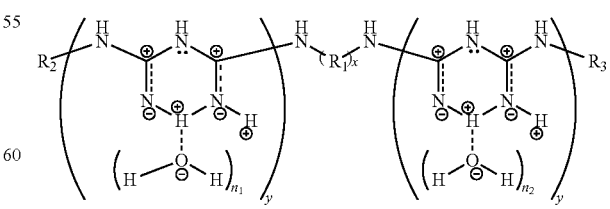

wherein $R_1$ comprises a straight chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group;

wherein $n_1$ and $n_2$, independent of each other, are numbers from 0 to 1; and wherein x and y, independent of each other, are numbers from 1 to 3000.

In certain embodiments, y is a number from 1 to 4, and x is a number from 1 to 100, from 1 to 20, from 1 to 10, or from 1 to 8. In one embodiment, the composition has a degree of hydration greater than 0 and less than 2y.

In one embodiment, the compound having the chemical Formula I comprises a bisguanide hydrate in which $n_1$ and $n_2$ are 1 having the chemical formula:

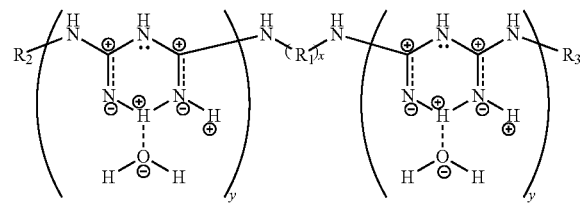

wherein $R_1$ comprises a straight chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group; and wherein x and y, independent of each other, are numbers from 1 to 3000. In some embodiments, y is a number from 1 to 4, and x is a number from 1 to 100, from 1 to 20, from 1 to 10, or from 1 to 8. In one embodiment, the composition has a degree of hydration greater than 0 and less than 2y.

In selecting suitable or viable substitutions, the functional group desirably does not eliminate or substantially impair the antimicrobial activity or chemical stability of the compound. For example, $R_1$ generally should not be an unsaturated compound because it would prevent the transfer of electrons via double or triple bonds, disturbing the tautomerism on each side of the bisguanide that is responsible for the partial charge of the guanide groups. $R_1$ may, however, include an isolated double or triple bond non-conjugated with other carbon atoms and with a single bond carbon atom (or more than one carbon atom) adjacent the guanide groups because the double or triple bond would not have electronic communication with the guanide groups and would not interfere with the tautomerism necessary for stabilization of the partial charges on each of the guanide groups. A further example relates to functional groups $R_2$ and $R_3$, which should be electron-withdrawing groups which are capable of assisting in the stabilization of the compound.

In one particular embodiment, the bisguanide hydrate of Formula I comprises chlorhexidine hydrate, having the chemical formula

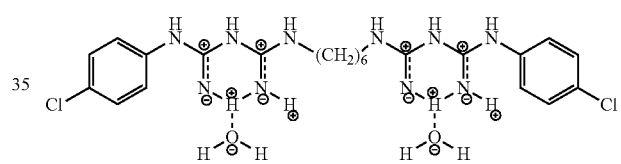

wherein $R_1$ is methylene, $R_2$ and $R_3$ each are a chlorophenyl, $n_1$ is 1, $n_2$ is 1, x is 6, and y is 1. In a particular embodiment, the composition has a degree of hydration that is greater than 0 and less than 2.

In another embodiment of the bisguanide hydrate of Formula I, $R_2$ and $R_3$, independent of one another, are electron-withdrawing groups.

In still other embodiments of the bisguanide hydrate of Formula I, $R_2$ and $R_3$ are independently aryls, are independently substituted aryls, or are independently phenyls. In another embodiment of the bisguanide hydrate of Formula I, $R_2$ and $R_3$ are independently substituted phenyls. The independently substituted phenyls may have ortho, para, or meta substitutions. The independently substituted phenyls may be identical to or different from one another.

In still another embodiment of the bisguanide hydrate of Formula I, $R_2$ and $R_3$ are independently substituted halo phenyls. The independently substituted halo phenyls may have ortho, para, or meta substitutions. The independently substituted halo phenyls may be identical to or different from one another.

In various other examples of the bisguanide hydrate of Formula I, $R_2$ and $R_3$ may independently be substituted halogens, substituted amines, substituted amides, substituted cyanos, or substituted nitros.

In other embodiments, the bisguanide compound includes the "neat" bisguanide composition having the chemical formula (Formula II):

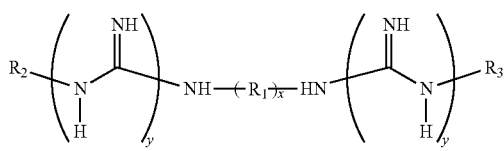

wherein $R_1$ comprises a straight, chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight, chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group;

wherein x and y, independent of each other, are numbers from 1 to 3000. In certain embodiments, y is a number from 1 to 4, and x is a number from 1 to 100, from 1 to 20, from 1 to 10, or from 1 to 8.

Where the bisguanide compound has at least four carbon-nitrogen double bonds (e.g., y≥2), hydrogen bonding results in the formation of a heterocyclic structure having the chemical formula of Formula III:

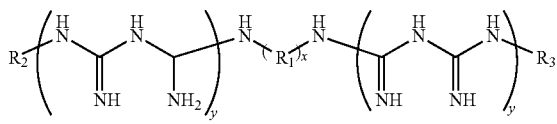

wherein $R_1$ comprises a straight, chained, branched, or cyclic alkyl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group; and wherein x and y, independent of each other, are numbers from 1 to 3000.

In a particular embodiment, the antimicrobial bisguanide compound of Formula III comprises chlorhexidine, a compound having the chemical formula

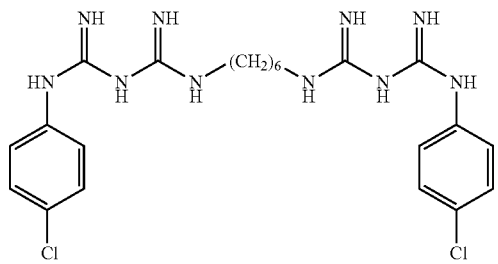

wherein $R_1$ is a methylene, $R_2$ and $R_3$ each are a chlorophenyl, x is 6, and y is 1.

Not wishing to be bound by any theory, it is believed that the antimicrobial bisguanide compounds provided herein form the heterocyclic ring structure below.

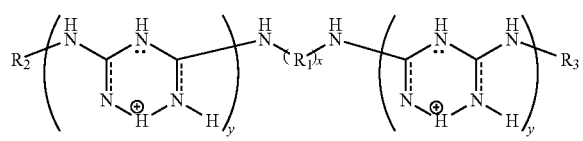

Accordingly, those skilled in the art will appreciate that the antimicrobial bisguanide compounds provided herein include their tautomers.

2. The Thermoplastic Polymer.

The thermoplastic polymer material of the antimicrobial polymeric material generally is selected taking into consideration its ability to form a molecular mixture. That is, the thermoplastic polymer and antimicrobial bisguanide should have sufficient molecular interactions with each other to permit distribution and immobilization of the antimicrobial bisguanide between the polymer chains. The molecular interactions, as used herein, include chemical interactions other than covalent bonds. Examples of such interactions include hydrogen bonding, Van der Waals forces, and other dispersive forces which would be expected between molecularly distributed compositions. In a preferred embodiment, the antimicrobial bisguanide and the thermoplastic polymer are substantially miscible with one another. In this way, the antimicrobial bisguanide can be distributed at the molecular level throughout the polymer. That is, the antimicrobial polymeric material may include a molecular mixture of these two components.

"Substantially soluble" or "substantially miscible" as used herein refers to the ability of the antimicrobial bisguanide to dissolve in a fluidized form of the thermoplastic polymer, such as a polymer melt, or in a solution of the polymer and an organic solvent. Thus, a "miscible blend" as used herein refers to a molecular mixture of two or more components.

Depending upon the process used to make the antimicrobial polymeric material, the melting temperature of the polymer may be an important factor in the selection of a suitable polymer material. In one embodiment, the melting temperature of the thermoplastic polymer must be such that the antimicrobial bisguanide compound is capable of mixing with the thermoplastic polymer when it is in its liquid state without being so high that the antimicrobial bisguanide degrades to a significant extent before the antimicrobial polymeric material can be cooled. In an embodiment, the thermoplastic polymer has a melting temperature below about 165° C., more particularly below about 135° C., and still more particularly below about 120° C. In other embodiments, the thermoplastic polymer may have a higher melting temperature if the polymer can be transformed into a liquid state without heating, e.g., by forming a solution with a suitable solvent, or if the heated polymer melt can be cooled rapidly enough following mixing.

Representative examples of suitable thermoplastic polymer materials include polyolefins, polyethylenes such as ethylene adipate, ethylene oxide, low density polyethylene, and high density polyethylene, and vinyl polymers such as ethyl vinyl ether, propyl vinyl ether, vinyl acetal, vinyl butyral, and butyl vinyl ether.

One of skill in the art can readily select other suitable polymers for use in the present antimicrobial polymeric materials, for example, by taking into consideration the component selection characteristics and antimicrobial polymeric material features described above. Those skilled in the art will appreciate that the solubility of two or more components may be determined using empirical models which evaluate the intermolecular forces between the solvent and the solute and the entropy change accompanying the solvation. For example, the Hansen Solubility Parameters of each component may be calculated from three-dimensional solubility coefficients which account for the dispersion bonds, polar bonds, and hydrogen bonds between molecules. The three parameters can be treated as coordinates for a point in three dimensions such that the nearer two molecules are in the three dimensional space, the more likely they are to dissolve in each other. The Hildebrand Solubility Parameter ($\delta$) also provides a means of evaluating the probable solubility of compositions, where materials with similar values of $\delta$ provide a good indication of solubility.

The antimicrobial bisguanide and thermoplastic polymer may be combined in any amounts in which the resulting polymer blend has sufficient antimicrobial activity while not substantially impairing the structural integrity of resulting polymer blend. Thus, the antimicrobial bisguanide should be present in an amount sufficient to facilitate contact between the antimicrobial bisguanide and the fluid in need of treatment. Those skilled in the art will appreciate, however, that the amount of antimicrobial bisguanide compound can be selected for use in the antimicrobial polymeric material, depending for example on the required mechanical characteristics (e.g., load bearing characteristics, porosity, etc.) that are specified for the particular fluid treatment application in which the antimicrobial polymeric material is to be used.

3. Additional Components in the Blend.

The antimicrobial polymeric material optionally may further include one or more additional components. In one embodiment, the additional component may be a plasticizer. These other components may be miscible or immiscible in the polymer-antimicrobial bisguanide blend.

The additional component may be in solid solution with the polymer. Alternatively, the additional component may be, for example, in particulate or fiber form. These other components may, for example, be useful in fluid purification, such as carbon, zeolites, etc. They may be homogeneously or heterogeneously distributed in the antimicrobial polymeric material. In one embodiment, the additional component is present in the antimicrobial polymeric material in an amount from about 0.1 wt % to about 20 wt. %. Those skilled in the art, however, will appreciate that the addition of one or more additional components should not substantially reduce the surface area of the antimicrobial bisguanide compound in the antimicrobial polymeric material or otherwise impair the antimicrobial activity of the antimicrobial polymeric material.

Methods for Making the Antimicrobial Polymer Materials

The antimicrobial bisguanide and thermoplastic polymer may be combined by any suitable means known to those of ordinary skill in the art. Such methods should allow for preparation of a substantially miscible blend in which the antimicrobial bisguanide is substantially undegraded.

In one embodiment, a method for preparing the antimicrobial polymeric materials comprises melting an antimicrobial bisguanide compound and a thermoplastic polymer with which the antimicrobial bisguanide compound is miscible; mixing the melted antimicrobial bisguanide compound and the melted thermoplastic polymer to form a miscible blend of the antimicrobial bisguanide compound dispersed in the thermoplastic polymer; and cooling the miscible blend to solidify the blend.

The thermoplastic polymer and antimicrobial bisguanide compound may be melted using any suitable means known to those skilled in the art as long as the antimicrobial bisguanide compound and thermoplastic polymer remain substantially undegraded. That is, the processing temperature must be sufficiently high to melt the thermoplastic polymer without being so high that the antimicrobial bisguanide compound degrades to a significant extent before the antimicrobial polymeric material can be cooled. In one embodiment, the thermoplastic polymer is melted by heating the thermoplastic polymer above its melting temperature, and the antimicrobial bisguanide compound may be mixed with the melted thermoplastic polymer to form a miscible blend of the antimicrobial bisguanide compound dispersed in the thermoplastic polymer. For example, the thermoplastic polymer and antimicrobial bisguanide compound may be blended before or after melting the thermoplastic polymer and antimicrobial bisguanide compound, as illustrated in FIGS. 4A and 4B.

In another embodiment, the thermoplastic polymer is dissolved in a suitable solvent and blended with the antimicrobial bisguanide compound. Because of the substantial insolubility of the antimicrobial bisguanide compound, however, such methods may still require heating of the antimicrobial bisguanide compound in order to obtain a miscible blend of the antimicrobial bsiguanide compound dispersed in the thermoplastic polymer. Methods for solvent casting of thermoplastic polymers are well known to those skilled in the art.

Figure 5:
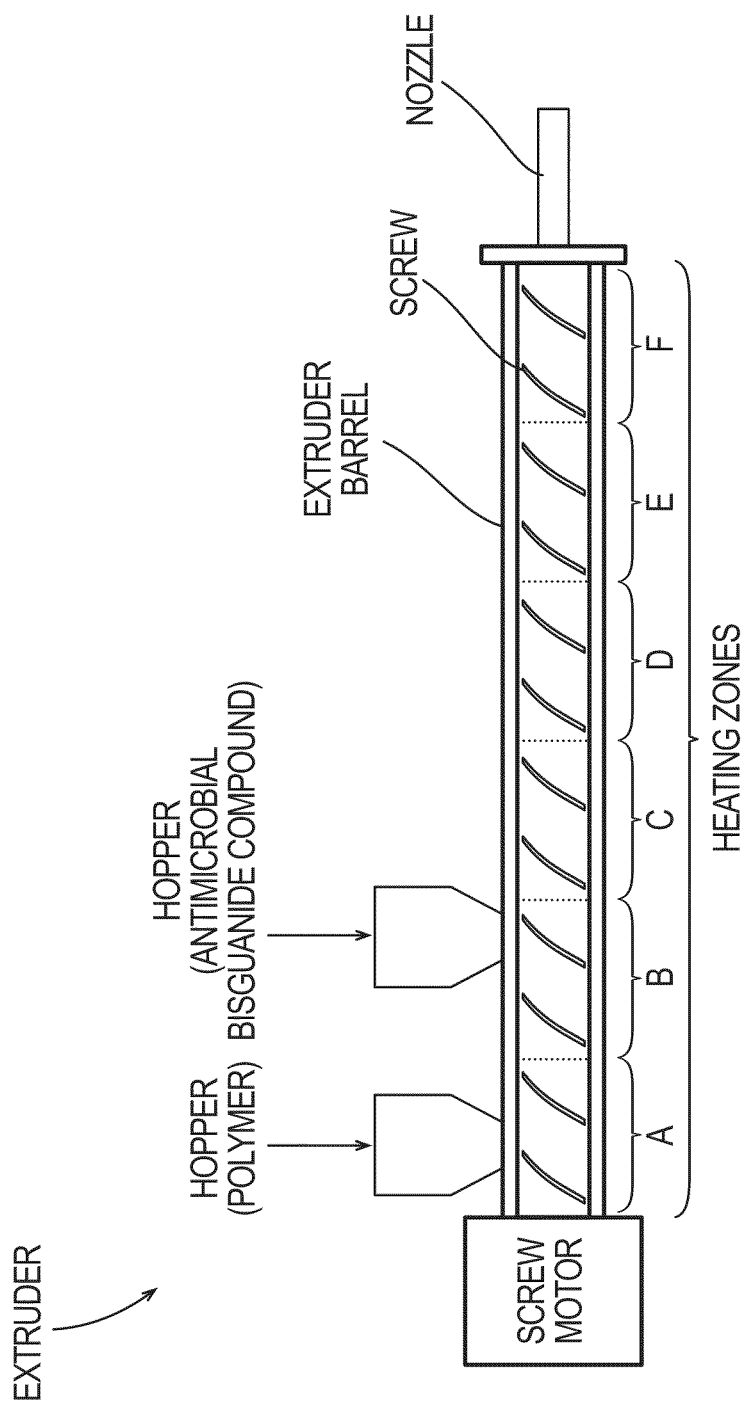
FIG. 5 is an illustration of an extrusion process for preparing an antimicrobial polymeric material according to an embodiment.

In an exemplary embodiment, the method for preparing an antimicrobial polymeric material comprises the extrusion process illustrated in FIG. 5. The extrusion process generally comprises feeding the thermoplastic polymer to the extruder and heating the thermoplastic polymer above its melting temperature to obtain a thermoplastic polymer melt, adding an insoluble antimicrobial material to the thermoplastic polymer melt and vigorously mixing to molecularly disperse the antimicrobial material throughout the thermoplastic polymer, and cooling the temperature of the heated blend to obtain a solid antimicrobial polymeric material. The mixing of the mixture and speed at which the mixture is passed through the extruder may be controlled by modifying the rate of rotation of the rotating screw in the extruder.

The heating profile of the extruder may be controlled using multiple independent controlled heater zones to gradually increase the temperature of the melt and minimize the length of time the mixture is exposed to higher temperatures, thereby minimizing the potential for degradation of the antimicrobial bisguanide compound. Generally, extruders comprise three or more independently controlled heater zones.

The porosity and structure of the antimicrobial polymeric material may be modified during the extrusion process. By increasing the porosity of the antimicrobial polymeric material, the surface area of the antimicrobial bisguanide compound that is exposed also may be increased, thereby enhancing the antimicrobial activity of the antimicrobial polymeric material. For example, use of a blowing agent (e.g., physical or chemical blowing agents, non-limiting examples of which include inert gases such as air and nitrogen) may promote the formation of small voids within the antimicrobial polymeric material. Such voids, however, should not substantially impair either the physical integrity of the antimicrobial polymeric material or the overall surface charge of the antimicrobial polymeric material.

In a particular embodiment, the resulting antimicrobial polymeric material is further processed into particles using methods well known in the art. For example, the polymer blend may be pulverized to obtain particle sizes which are suitable for the desired use, using various size reduction equipment known in the art including, but not limited to, mills, grinders, and the like. In one embodiment, the cooled antimicrobial polymeric material is pulverized to a desired particle size by means of a blender. In another embodiment, the particles is pulverized to a desired particle size using cryogenic methods.

Figure 6A:
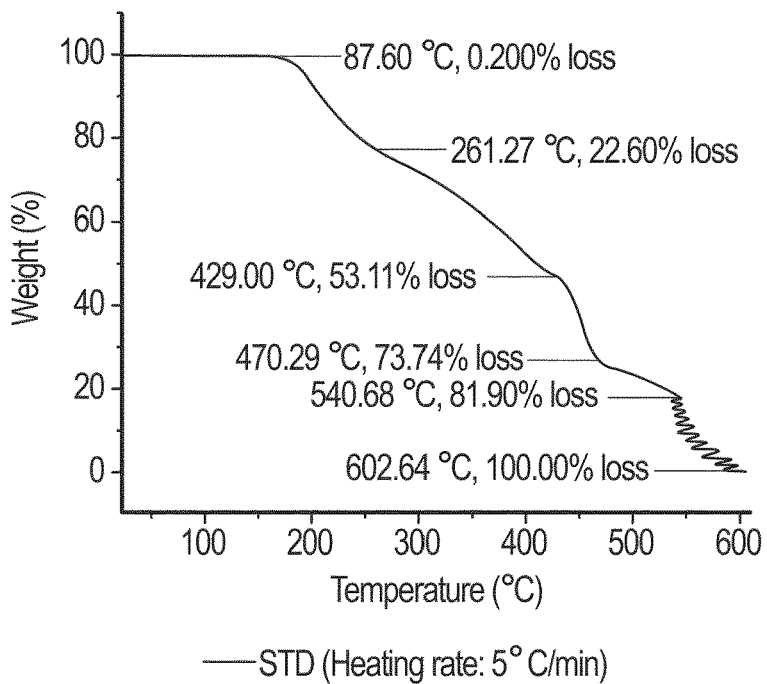
FIGS. 6A and 6B are TGA thermograms of chlorhexidine and chlorhexidine hydrate.
Figure 6B:
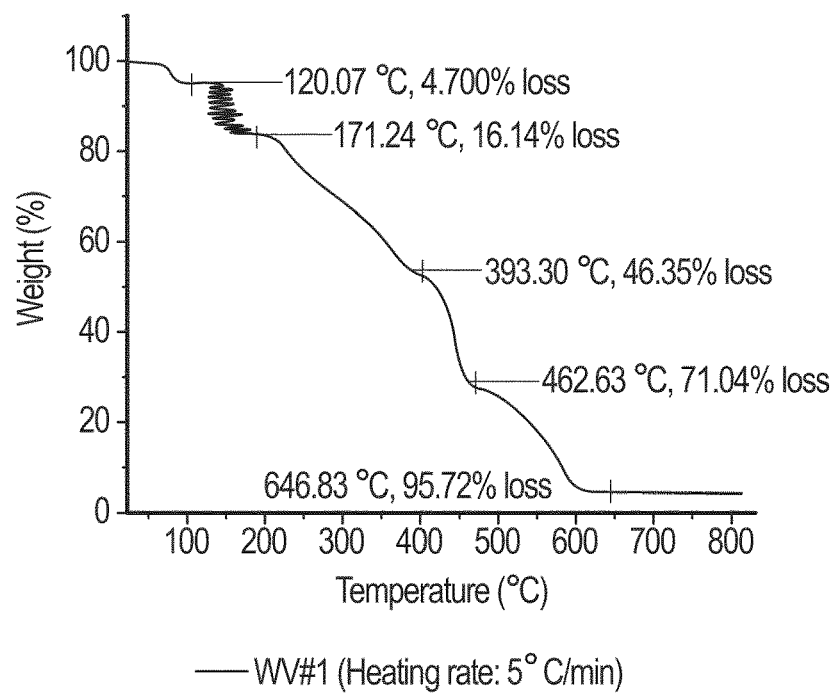
Figure 7A:
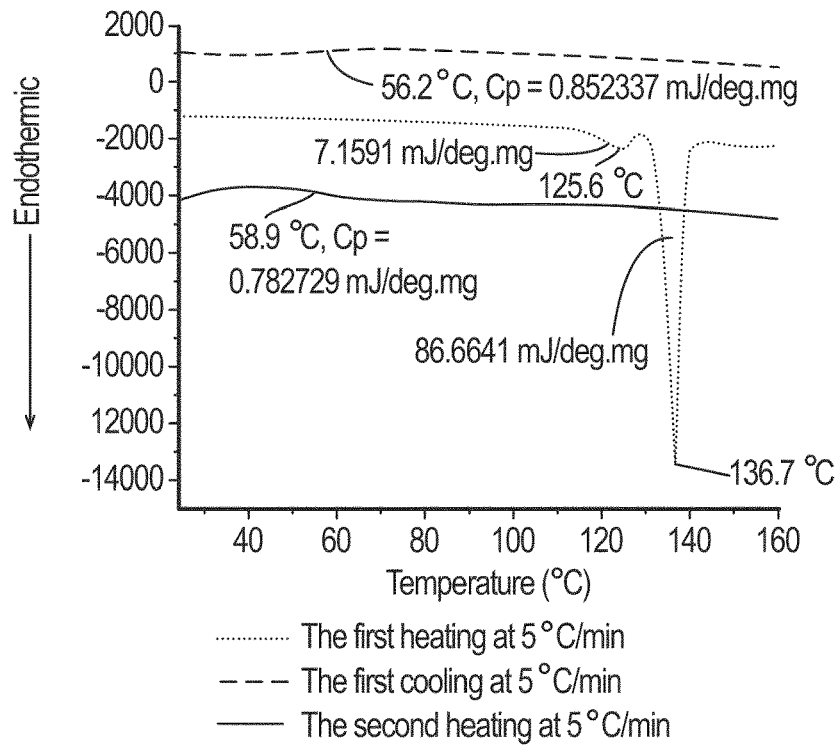
FIGS. 7A and 7B are DSC thermograms of chlorhexidine and chlorhexidine hydrate.
Figure 7B:
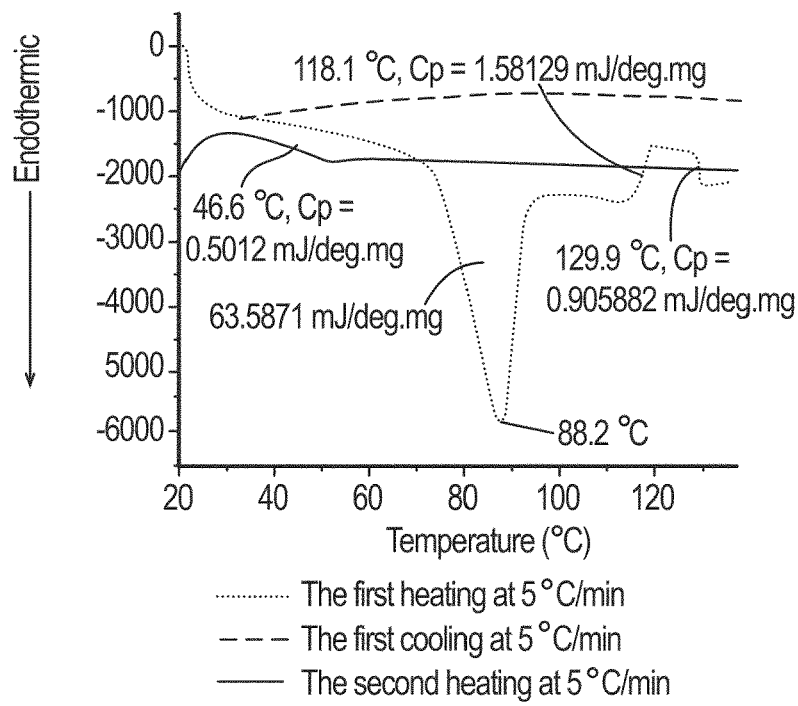

In exemplary embodiments, the resulting antimicrobial polymeric material is further processed into suitable structures by any suitable means known to those in the art (e.g., molding, die casting, etc.). For example, in one embodiment the antimicrobial polymeric material is molded into a suitable monolithic porous structure. In another embodiment, the antimicrobial polymeric material is formed into fibers (e.g., nonwoven or woven materials). The processing temperature of any molding process should be sufficiently below the degradation temperature of the antimicrobial bisguanide compound such that there is substantially no degradation of the antimicrobial bisguanide compound. The degradation temperature of the antimicrobial bisguanide compounds may be evaluated by considering the TGA and DSC thermograms of the antimicrobial bisguanide compound. Illustrative TGA thermograms (FIGS. 6A and 6B) and DSC thermograms (FIGS. 7A and 7B) of chlorhexidine and chlorhexidine hydrate, respectively, are provided.

Applications/Uses for the Antimicrobial Devices

The compositions and treatment devices described herein have numerous applications. Advantageously, the treatment devices are of a nonsoluble and nonconsumable catalytic nature, and may be capable of inactivating a broad spectrum of microorganisms. Generally, the compositions and purification materials can be used in applications where it is desirable to reduce and/or eliminate microorganisms in a fluid. Nonlimiting examples of such fluids include aqueous solutions, water, air, and other gases.

In a particular embodiment, the antimicrobial polymeric materials described herein are incorporated into treatment devices for water purification. Such treatment devices may be installed at the point of use. This may eliminate the need for chlorination of water supplies to protect against contamination of microorganisms.

In another embodiment, the purification material may be portable for obtaining potable drinking water at any time or place. These devices would be especially desirable in undeveloped countries where one of the greatest needs is potable drinking water.

The purification material and method are particularly useful in those applications where the required reduction in the concentration of microbiological contaminants significantly exceeds the U.S. EPA standards for microbiological water purification devices. In one embodiment, the microbiological contaminants are inactivated when a fluid is forced through the purification material by a difference in pressure on the influent and effluent sides or by a vacuum on the effluent side, of the purification material.

In addition to functioning as a purifier for drinking water, the purification material may be used to purify water used for recreational purposes, such as water used in swimming pools, hot tubs, and spas, allowing the chlorine normally required to eliminate living microorganisms to be either reduced or completely eliminated.

In one embodiment, the present antimicrobial polymeric materials and devices can be used for low-temperature sterilization techniques, eliminating the need for techniques requiring elevated temperatures and pressures, such as pasteurization. This would prove especially useful for both the food and beverage industries.

Because the purification material efficiently inactivates microorganisms in aqueous solutions, it also has numerous applications in the pharmaceutical and medical fields. For example, the purification material may be used to inactivate microorganisms in certain physiological fluids or in devices, e.g., at-home dialysis machines.

In another embodiment, the antimicrobial polymeric materials and devices can be used in hospital or industrial areas requiring highly purified air having extremely low amounts of microorganisms, e.g., intensive care wards, operating rooms, clean rooms used for care of immunosuppressed patients, or industrial clean rooms for manufacturing electronic and semiconductor equipment. The purification materials also can be used for residential air-purification. Such applications would be especially useful for individuals who suffer from heightened reactivity to air-borne microorganisms. In yet another embodiment, the purification material can may be used to augment protection for humans or animals against air-borne microorganisms released in a bioterrorist attack.

In one particular application, the antimicrobial polymeric materials may be incorporated into a device designed to eliminate pathogenic protozoa (e.g., of the genus *Plasmodium* and phylum Apicomplexa) that cause diseases such as malaria. Malaria is typically transmitted to humans through mosquitoes and remains a leading cause of death in undeveloped countries. Mosquitoes are infected with the protozoa from water reservoirs and lakes where the mosquitoes breed. Eliminating the protozoa from the breeding habitats of the mosquitoes may help eliminate outbreaks of malaria.

Numerous other applications exist for which the present antimicrobial polymeric materials and purification materials can be used. Representative examples include the treatment of water used in cooling systems, fermentation applications and cell culture, and inactivation of microorganisms in gases (e.g., anesthetics, carbon dioxide used in carbonated beverages, gases used to purge process equipment, etc.).

In each of these applications, the method of using the present antimicrobial polymeric materials and purification materials is relatively simple: The fluid to be treated is brought into physical contact with the antimicrobial polymeric materials. Typically, the fluid will be forced from one side of the porous purification material through to the other side of the purification material due to a pressure drop across the purification material. The pressure driven flow can be conducted using conventional fluid pumps or gravity fed.

The antimicrobial polymeric materials provided herein also may be used for numerous alternative uses (i.e., unrelated to fluid treatment) in which it is desirable to have antimicrobial properties. For example, in one embodiment the antimicrobial polymeric materials may be utilized in medical devices to minimize the risk of contamination. Non-limiting examples of such devices include bandages for wound treatment on which the antimicrobial polymeric material is coated onto or incorporated into, stents, catheters, or other implantable medical devices (e.g., dental implants, prosthetic joints, etc.). For example, the antimicrobial polymeric material may be processed into a woven or non-woven fiber form for forming a flexible porous sheet that can be incorporated into a bandage or gauze. Those of skill in the art will appreciate that in such applications it may be desirable to select the polymeric material based on its biocompatibility. In another embodiment, the antimicrobial polymeric materials may be utilized as coatings on surfaces or in substantially impermeable monolithic structures in which antimicrobial activity would be desirable. Non-limiting examples of such devices include coatings on surfaces such as walls, plumes, and vents.

The devices, compositions, and methods described above will be further understood with reference to the following non-limiting examples.

Example 1: Preparation of a Polyethylene Blend

A 150 mL beaker was equipped with a mechanical stirrer and placed in an oil bath equipped with a thermostat. A specified amount of a low density polyethylene (LDPE) was placed into the beaker and heated to 150° C. with stirring. A specified amount of chlorhexidine hydrate was added to the melted polyethylene, heated for an additional 10 minutes with stirring, and then cooled to room temperature. The resulting mixture cooled to a hard, white solid that was collected, pulverized in a laboratory blender, and placed in a glass vial covered with argon gas.

The amounts of the polyethylene and chlorhexidine hydrate used in each sample are set forth below.

TABLE 1

Composition of blend samples

| Sample | Polyethylene mass (% by weight) | Chlorhexidine Hydrate mass (% by weight) |
|---|---|---|
| 1 | 28.5 (95) | 1.5 (5) |
| 2 | 27.0 (90) | 3.0 (10) |
| 3 | 25.5 (85) | 4.5 (15) |
| 4 | 24 (80) | 6 (20) |

Example 2: Preparation of a Polystyrene Blend

A 150 mL beaker was equipped with a mechanical stirrer and placed in an oil bath equipped with a thermostat. A specified amount of polystyrene (PS) was placed into the beaker and heated to 210° C. with stirring. Upon heating, the polystyrene was white with a slight discoloration due to thermal decomposition. A specified amount of chlorhexidine hydrate was added to the melted polystyrene, heated for an additional 10 minutes with stirring, and then cooled to room temperature. The resulting mixture cooled to a hard, white solid (with discoloration) that was collected, pulverized in a laboratory blender, and placed in a glass vial covered with argon gas.

The amounts of the polystyrene and chlorhexidine hydrate used in each sample are set forth below.

TABLE 2

Composition of blend samples

| Sample | Polystyrene mass (% by weight) | Chlorhexidine Hydrate mass (% by weight) |
|---|---|---|
| 1 | 28.5 (95) | 1.5 (5) |
| 2 | 27.0 (90) | 3.0 (10) |
| 3 | 25.5 (85) | 4.5 (15) |
| 4 | 24 (80) | 6 (20) |

Although soluble and effective for forming a polymer matrix with the chlorhexidine hydrate, the processing temperature for polystyrene (PS) was too high and caused a yellowing color due to the partial thermal decomposition of the bisguanide. Although processing of the polyethylene and chlorhexidine hydrate blend on a lab scale did not immediately cause discoloration, extrusion on a larger scale (75 lbs.) caused some slight yellowing effect in the appearance, indicating there was at least some degradation of the antimicrobial bisguanide compound and that the processing temperatures needed to be further optimized.

Example 3: Preparation of Polyurethane Blends

Polyurethanes also were combined with chlorhexidine hydrate using methods similar to those described in Examples 1 and 2. However, these polymers and the antimicrobial bisguanide compound did not form the molecular distribution due to a lack of molecular interaction between the two components. As a result, clumps of the bisguandide compound were formed. Thus, the blended product was not a miscible blend.

Example 4: Formation of Particulate Forms of the Antimicrobial Material

Antimicrobial polymeric materials were prepared using a commercial extruder (Wernes Phleidere Twin Screw Extruder ZSK 30, D=30 mm, L/D=5) with an automatic feeder for resin (K-Tron single-screw, Model K2U-T35) and a separate feeder for chlorhexidine (K=Tron feed, single screw) to obtain a strand of extrudate from the die. The extruder included six temperature zones, with the zone nearest the hopper having a temperature of approximately 100° C. and the remaining five temperature zones having temperatures of about 150° C.

The thermoplastic polymer was the same low density polyethylene (LDPE) as set forth in Example 1. The chlorhexidine was fed into the extruder in an amount sufficient to provide 5% by weight of the extruded resin. The strand of extrudate was chopped to provide an average diameter of 80 mesh pellets.

Example 5: Preparation of a Polyolefin Elastomer Blend

Figure 8A:
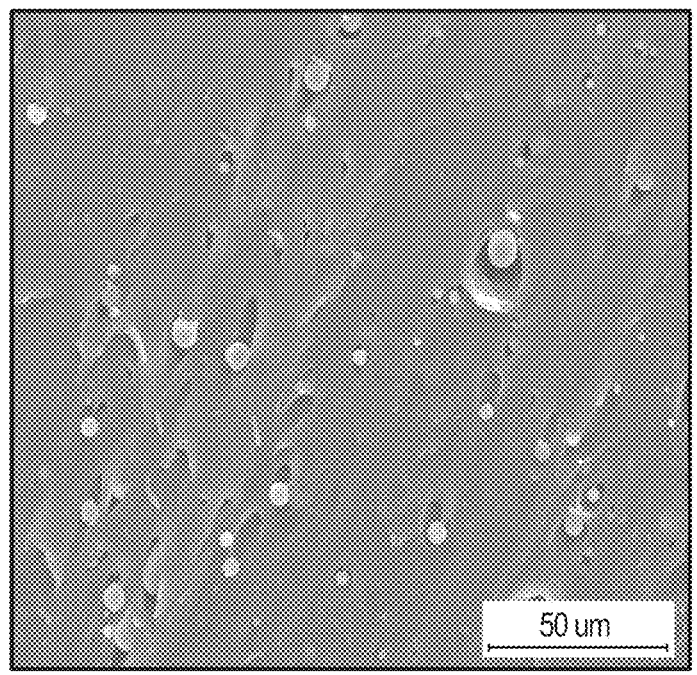
FIGS. 8A and 8B are SEM images of a mixture of chlorhexidine and resin.
Figure 8B:
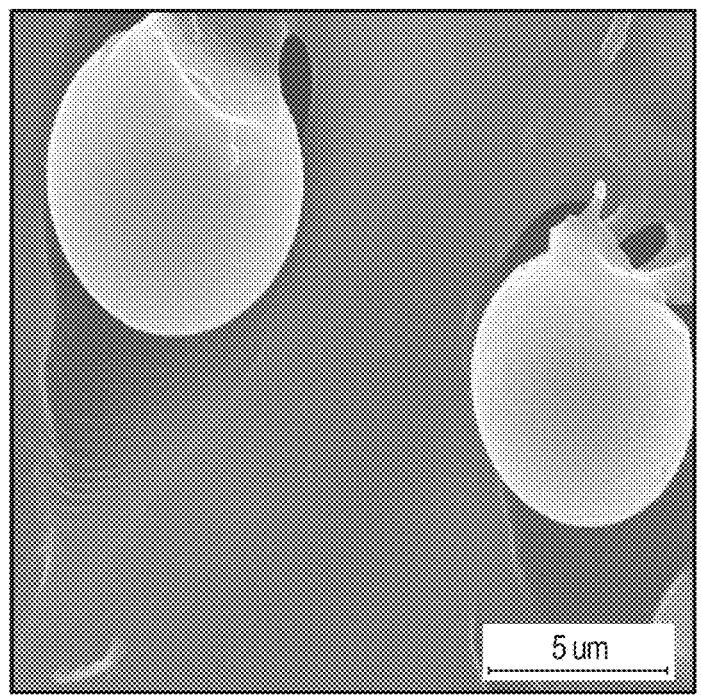

To avoid the thermal decomposition of the chlorhexidine hydrate, a lower temperature polyolefin elastomer type resin (DOW Engage™ 8411) was used to prepare pellets in a commercial extruder. The chlorhexidine hydrate was fed into the extruder described in Example 4 in an amount sufficient to provide 10% by weight of the extruded pellet. The pellets were pulverized cryogenically (liquid nitrogen) to provide an average of 20 mesh particles. Although the chlorhexidine hydrate melted, it did not solubilize within the resin to form a miscible blend. The SEM micrographs (FIGS. 8A and 8B) of the resulting resin illustrate the failure of the chlorhexidine to form a solid solution with the resin.

Example 6: Antimicrobial Testing

The polymer blends prepared in Examples 1, 4, and 5 hereinabove were pulverized to obtain from 325 to 20 mesh particle sizes and tested for antimicrobial activity using colonized *E. coli* dispersions. The particles were packed in a 12.0 in ×1.0 in diameter acrylic tube to obtain a particle bed thickness of 0.5 in, 1.0 in, 1.5 in, or 2.0 in. A liquid culture of *E. coli* ($10^8$ CFU concentration) was allowed to flow through the packed tube under gravity flow and at STP conditions. Although the flow rate was barely a steady stream, it was sufficient to evaluate the antimicrobial activity of the polymer blends.

Bacterial recovery was determined by Aerobic Plate Count and is shown in Table 3. The total reduction in bacterial growth was obtained by subtracting the log of the number of colony forming units per mL (CFU/mL) of the effluent samples by the log of the number of CFU/mL of the control.

TABLE 3

Reduction of Bacterial Growth Using Antimicrobial Polymeric Materials

| Purification Material (Thickness, in) | Initial Bacteria (CFU/mL) | Log | Effluent Bacteria (CFU/mL) | Log | Log Reduction in Bacteria |
|---|---|---|---|---|---|
| Chlorhexidine (5%)-LDPE (Lab-Scale - 1.0 in) | $237 \times 10^8$ | 10.37 | $25 \times 10^3$ | 4.40 | 5.98 |
| Chlorhexidine (5%)-LDPE (Extruder - 0.5 in) | $9 \times 10^9$ | 9.95 | $1 \times 10^2$ | 2.00 | 7.95 |
| Chlorhexidine (5%)-LDPE (Extruder - 1.0 in) | $9 \times 10^9$ | 9.95 | $3.7 \times 10^3$ | 3.57 | 6.38 |
| Chlorhexidine(5%)-LDPE (Extruder - 2.0 in) | $9 \times 10^9$ | 9.95 | $1 \times 10^2$ | 2.00 | 7.95 |
| Chlorhexidine (10%)-Engage (Extruder - 1.0 in) | $1.07 \times 10^7$ | 7.03 | $1 \times 10^1$ | 1.00 | 6.03 |
| Chlorhexidine (10%)-Engage (Extruder - 1.5 in) | $1.07 \times 10^7$ | 7.03 | $3 \times 10^1$ | 1.48 | 5.55 |
| Chlorhexidine (10%)-Engage (Extruder - 2.0 in) | $1.07 \times 10^7$ | 7.03 | $3 \times 10^1$ | 1.48 | 5.55 |

There was an approximately Log-6 to Log-8 reduction of the *E. coli* which was passed through the packed tubes of the chlorhexidine-low density polyethylene alloys, whereas there was only a Log-5.5 reduction of the *E. coli* was observed with the packed tubes of the chlorhexidine-Engage™ alloys at a higher concentration of the chlorhexidine. Not wishing to be bound by any theory, it is believed that the enhanced antimicrobial activity may be attributed to the immobilization of the antimicrobial bisguanide compound as a molecular blend within the polymer.

Figure 9A:
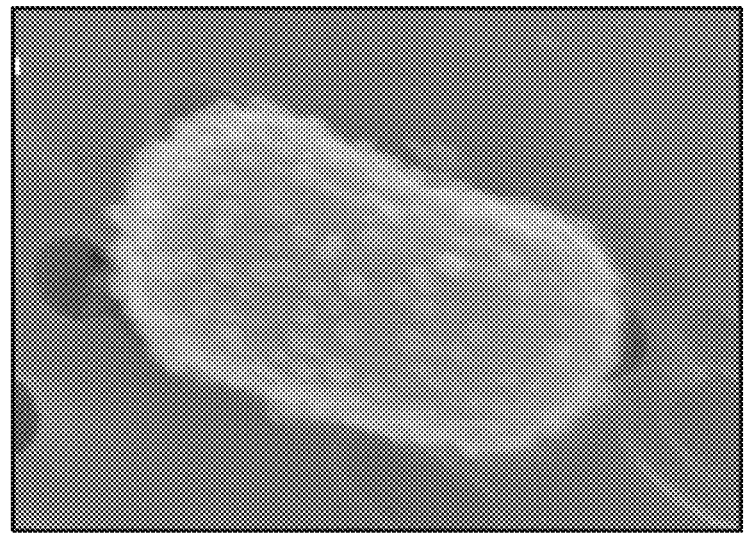
FIGS. 9A and 9B are SEM images of E. coli cells exposed to an antimicrobial polymer material according to an embodiment.
Figure 9B:
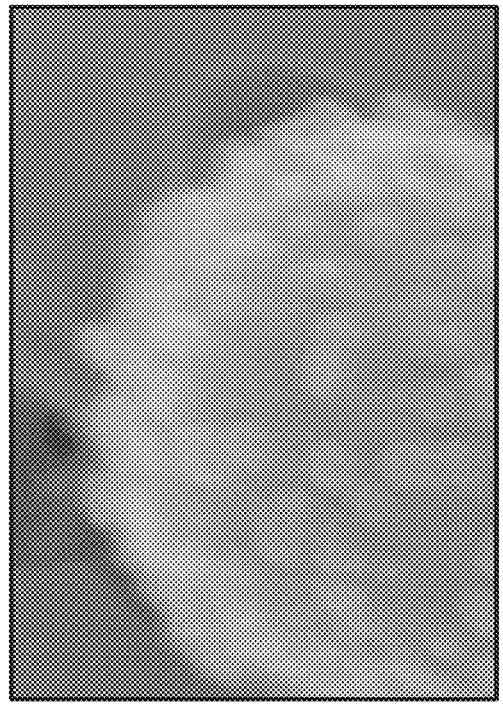

An SEM micrograph of a dead *E. coli* cell, shown in FIGS. 9A and 9B, illustrates the surface-dependent mechanism of the antimicrobial polymer material's antimicrobial activity. The sites of collision with the chlorhexidine in the polymer blend are visible and appear to have caused disassembly on the cell wall. Not wishing to be bound by any theory, it is believed that the cell wall was pulled apart upon collision via Brownian motion with the surfaces of the antimicrobial polymer blend. The cell wall is further magnified in FIG. 9B, where the frayed fibrous cell wall material can be observed.

Figure 10:
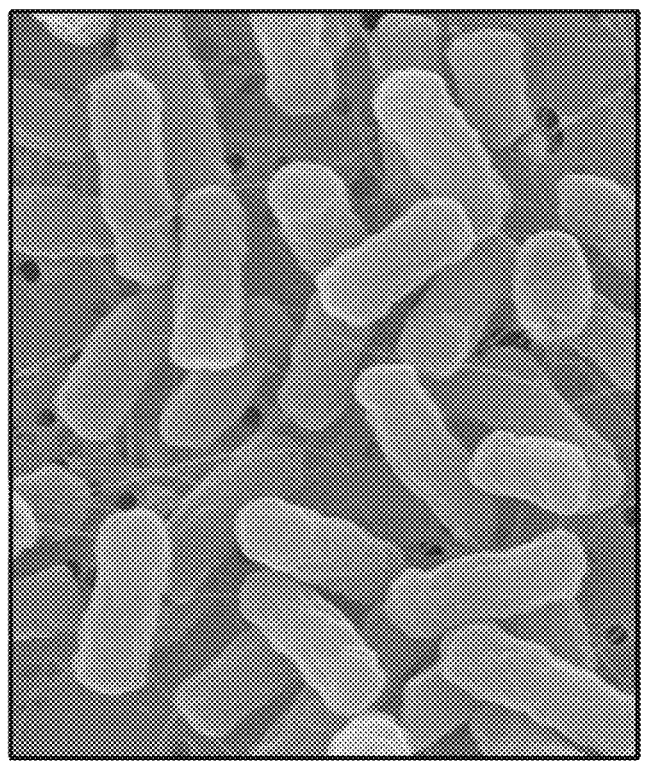
FIG. 10 is an SEM image of E. coli cells exposed to conventional antimicrobial materials.

Generally, a typical dead *E. coli* cell (FIG. 10) does not show any change in its surface morphology except for possible shrinkage due to loss of cytoplasm. This mechanism of activity generally is attributed to a soluble oxidant or surface active agent, such as a soluble chlorhexidine salt, that undergoes a second order chemical reaction (i.e., the agent is consumed in a stoichiometric type relationship). The antimicrobial polymer blend, conversely, appears to react catalytically with the microorganisms and is not consumed during the reaction.

Example 7: Analysis of Leaching

The effluent water stream from Example 6 also was tested by a standard HPLC method to evaluate the amount, if any, of the antimicrobial bisguanide that may have leached into the effluent water. Less than 2 ppm of the insoluble antimicrobial bisguanide compound was detected in the effluent of the low density polyethylene alloys produced on the lab scale, while less than 1 ppm of the insoluble antimicrobial bisguanide compound was detected in the effluent of the low density polyethylene alloys produced on the production scale. These extremely low concentrations indicate advantageously that substantially all of the insoluble antimicrobial bisguanide compound remained distributed within the polymer blend. Effluent water streams from testing conducted using a low density polyethylene alloy having 10% by weight chlorhexidine produced on the production scale had approximately 96 ppb of the insoluble antimicrobial bisguanide compound. Conversely, over 20 ppm of the insoluble antimicrobial bisguanide compound was detected in the effluent of the Engage™ blends, indicating that the antimicrobial bisguanide compound was not immobilized within the polymer blend.

Distilled water was flowed through the tubes after the foregoing experiments to determine whether there was a soluble portion of the insoluble antimicrobial bisguanide which was responsible for the observed antimicrobial activity which is common with soluble antimicrobial bisguanide salts (e.g., chlorhexidine gluconate). The results were negative for each of the low density polyethylene alloys.

Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

What is claimed is:

1. An antimicrobial composition comprising:
a solid miscible blend of chlorhexidine and low density polyethylene with a melting temperature below about 165° C., wherein the low density polyethylene and the chlorhexidine are melted and blended together, and the solid miscible blend is from 5% to 15% by weight chlorhexidine and the chlorhexidine is distributed at the molecular level within the low density polyethylene, and immobilized within the solid miscible blend, wherein the solid miscible blend is substantially free of degraded chlorhexidine.

2. The antimicrobial composition of claim 1, wherein the chlorhexidine is in an amorphous form.

3. The antimicrobial composition of claim 1, wherein the miscible blend is in the form of particles, fibers, or a combination thereof.

4. The antimicrobial composition of claim 1, wherein the miscible blend is in the form of an aggregation or collection of particles, the particles having a volume average diameter from about 400 mesh (37 micron) to about 20 mesh (840 micron).

5. The antimicrobial composition of claim 1, wherein the miscible blend is in the form of a porous monolithic structure.

6. The antimicrobial composition of claim 5, wherein the porous monolithic structure comprises a sintered disk, block, tube, or cylinder.

7. The antimicrobial composition of claim 1, wherein the miscible blend is in the form of a nonwoven material.

8. An antimicrobial composition comprising:
a solid miscible blend of chlorhexidine and low density polyethylene, wherein the low density polyethylene and the chlorhexidine are melted and blended together, and the solid miscible blend is from 5% to 15% by weight chlorhexidine and the chlorhexidine is distributed at the molecular level within the low density polyethylene, and immobilized within the solid miscible blend, wherein the solid miscible blend is substantially free of degraded chlorhexidine and is characterized by a minimum 6-log reduction of bacteria from an influent concentration of $1\times10^7$ per 100 mL water.

* * * * *